United States Patent [19]
Hisata et al.

[11] Patent Number: 5,553,499
[45] Date of Patent: Sep. 10, 1996

[54] ULTRASONIC MICROSCOPE HAVING AN AUTOMATIC FOCUSING ADJUSTMENT MECHANISM

[75] Inventors: Nahoko Hisata; Tomio Endo, both of Hachiouji, Japan

[73] Assignee: Olympus Optical Co., Ltd., Tokyo, Japan

[21] Appl. No.: 300,064

[22] Filed: Sep. 2, 1994

Related U.S. Application Data

[63] Continuation of Ser. No. 835,460, filed as PCT/JP91/01191, Sep. 7, 1991 published as WO92/04628, Mar. 19, 1992, abandoned.

[30] Foreign Application Priority Data

Sep. 7, 1990 [JP] Japan .................................. 2-238010
Sep. 7, 1991 [WO] WIPO ....................... PCT/JP91/01191

[51] Int. Cl.[6] ................................................ G01N 29/04
[52] U.S. Cl. ............................... 73/606; 73/611; 73/613; 73/620; 73/631; 73/634
[58] Field of Search ............................ 73/606, 611, 613, 73/620, 631, 634

[56] References Cited

U.S. PATENT DOCUMENTS 4,683,751  8/1987  Imade et al. ............................... 73/606

FOREIGN PATENT DOCUMENTS 0121890  10/1984  European Pat. Off. .
3835886A1  4/1990  Germany .
58-39942  3/1983  Japan .
62-249054  10/1987  Japan .

*Primary Examiner*—Hezron E. Williams
*Assistant Examiner*—Richard A. Moller
*Attorney, Agent, or Firm*—Frishauf, Holtz, Goodman, Langer & Chick

[57] ABSTRACT

Ultrasonic wave converged by an acoustic lens is made incident onto a sample and wave reflected from the sample is received and converted into received electric signal by a transducer. A part of this electric signal is picked up by a gate section and the signal thus picked up is applied to an attenuator where it is converted into a variable ratio of input to output. The strength of the signal thus gain-adjusted is compared with a threshold value by a comparator. Responsive to the comparison result thus obtained, the gain of the attenuator is adjusted to make the input/output ratio of the attenuator a desired value. A computer calculates the focus position of the acoustic lens from a gain curve of the attenuator changing when the acoustic lens is moved from a position, remote enough from its focus position, to the sample. Drivel signal responsive to the result thus calculated is applied to a Z-drive control section. As the result, the distance of the acoustic lens relative to the sample is adjusted to bring the acoustic lens to the focus position.

2 Claims, 3 Drawing Sheets

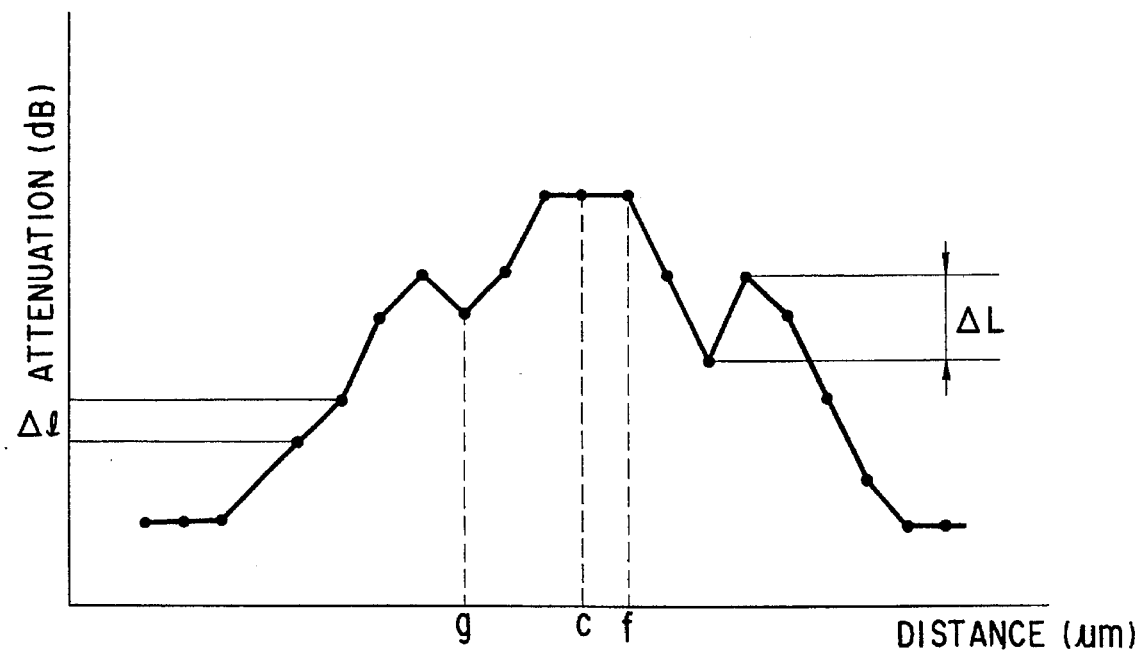
F I G. 3
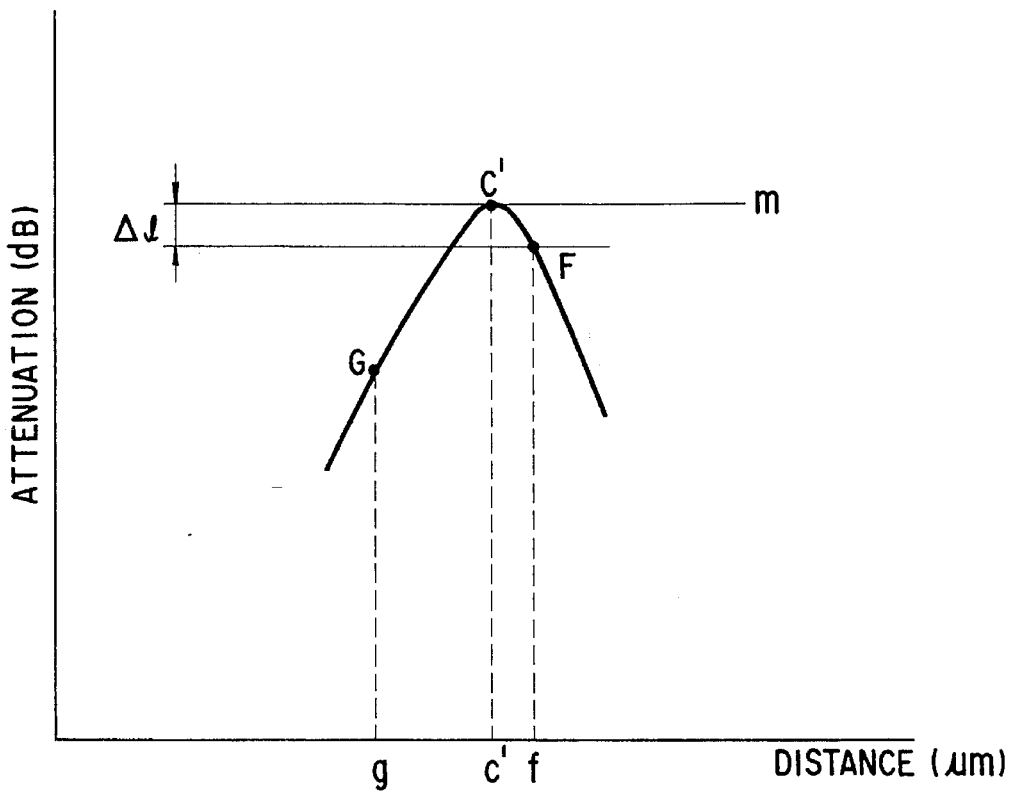
F I G. 4

ULTRASONIC MICROSCOPE HAVING AN AUTOMATIC FOCUSING ADJUSTMENT MECHANISM

This application is a continuation, of application Ser. No. 07/835,460, filed as PCT/JP91/01191, Sep. 7, 1991, published as WO92/04628, Mar. 19, 1992, now abandoned.

FIELD OF THE INVENTION

The present invention relates to an ultrasonic microscope for viewing the surface and inside of a sample using ultrasonic pulses.

BACKGROUND OF THE INVENTION

In conventional ultrasonic microscopes, an acoustic lens is used. An ultrasonic wave is focused into a micro-spot and directed to a sample through the acoustic lens. A reflected wave from the sample is received and converted into a received electric signal. A part of this received signal is gated to pick up a portion of the sample-reflected wave. The peak value of the sample-reflected wave component thus picked up is detected to obtain a piece of information relating to a point on the sample. When this process is carried out while scanning the sample with ultrasonic waves and in the horizontal direction, the ultrasonic wave image of the sample can be obtained.

The peak value or strength of the detected value becomes the largest when the acoustic lens is focused on the sample. Some automatic focusing methods of the acoustic lens which use this fact have been proposed. In a case where the focal position of the acoustic lens is previously known, for example, the timing at which the reflected waves from the sample surface are received at the time the acoustic lens is focused can be calculated as a delay from the reference time such as the signal transmitting time. When the gating is carried out at this timing, therefore, the reflected wave from the sample can be picked up and its strength can be measured. The strength of the reflected wave from the sample is compared with a threshold value while moving the acoustic lens from a position remote enough from the sample to the sample. When these two values coincide with each other or the value measured exceeds the threshold value, the acoustic lens is stopped. The automatic focusing of the acoustic lens can be achieved in this manner.

The threshold value is made a little smaller than the strength of the reflected wave at the focus point. Using two gates, the threshold value is compared with peak values in the two gates. The automatic focusing of the acoustic lens can also be achieved in this manner. More specifically, the first gate is set at the time when the wave reflected from the sample surface at the focus point is received, and the second gate is set near this time. There are then used a circuit for checking that the strength of the detected signal of that reflected wave picked up by the first gate becomes larger than that picked up by the second gate, a circuit for checking that the strength of the detected signal at the first gate exceeds the threshold value, and an AND circuit for the outputs of the both circuits. The acoustic lens can be stopped responsive to output applied from the AND circuit.

In the case of the above-described focusing methods, however, it is necessary that the threshold value is set at a level near the strength of the reflected wave obtained at the time when the acoustic lens is focused on the sample. In addition, the threshold value must be adjusted to an appropriate level every time the sample is replaced by a new one because the strength of the reflected wave from the sample depends upon samples viewed.

The present invention is therefore intended to eliminate the above-mentioned drawback.

Accordingly, the object of the present invention is to provide an ultrasonic microscope, enabling the operator to more easily achieve automatic focusing but making it unnecessary for the operator to adjust the threshold value every time the sample is replaced by a new one.

SUMMARY OF THE INVENTION

An object of the present invention can be attained by an ultrasonic microscope wherein ultrasonic waves converged by an acoustic lens are made incident onto a sample. Reflected waves from the sample are received and converted into received electric signals, and the ultrasonic wave image of the sample is formed using the received signals. The ultrasonic microscope adjusts the distance of the acoustic lens relative to the sample, and picks up those of the received electric signals which correspond to a part of the reflected signals from the sample. A gain-adjusted output signal is applied from the pickup means and is compared with a previously-set threshold value. The gain of the gain-adjusted output signal is controlled on the basis of the obtained comparison values so as to bring the signal input/output ratio to an optional value. The focus position of the acoustic lens is determined on the basis of an attenuation curve obtained as an attenuation amount with regard to one position of the acoustic lens when the acoustic lens is moved from another position to the one position, remote from its focus position, to said sample and a drive signal, responsive to the result thus calculated, is outputted to set the distance adjustment.

According to the ultrasonic microscope of the present invention, a part of that electric signal which corresponds to the reflected wave from the sample is picked up by the pickup means and applied to the converter means. The strength of the signal gain-adjusted by the converter means is compared with the threshold value by the comparator means. The gain of the converter means is adjusted on the basis of the result obtained by this comparison so as to bring its input/output rate to a desired value. The focused position of the acoustic lens is calculated by the focus adjustment control means from a gain curve of the converter means which changes when the acoustic lens is moved from a position, remote enough from its focused position, to the sample. A drive signal which corresponds to the result thus calculated is applied to the distance adjuster means. As the result, the distance of the acoustic lens relative to the sample can be adjusted to make the acoustic lens focused on the sample.

BRIEF DESCRIPTION OF THE DRAWINGS

FIG. 3 is a view showing a computer-processed wave form representing the attenuation curve; and FIG. 4 is a graph intended to explain an approximation method employed in the focus position detecting calculation.

DETAILED DESCRIPTION OF THE INVENTION

An embodiment of the present invention will be described with reference to the accompanying drawings.

Figure 1:
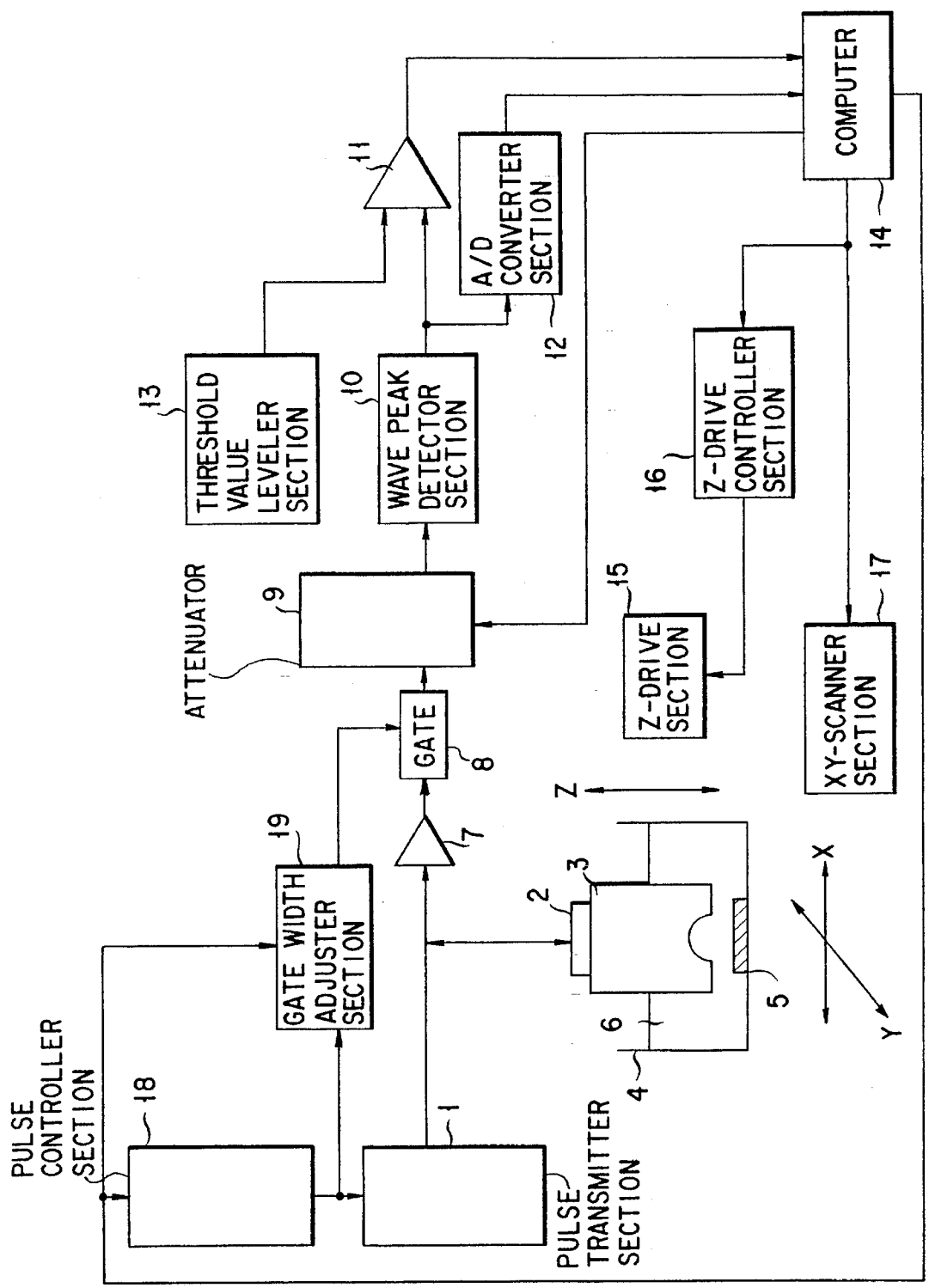
FIG. 1 is a block diagram showing the ultrasonic microscope according to an embodiment of the present invention.

FIG. 1 is a block diagram showing the ultrasonic microscope provided with an automatic focusing system according to an embodiment of the present invention. An ultrasonic pulse transmitting and receiving means comprises a pulse transmitter section 1, a transducer 2 for converting the pulse received from the pulse transmitter section 1 into an ultrasonic pulse, and an acoustic lens 3 for focusing the ultrasonic pulse created by the transducer 2 onto a sample 5 as a microspot. A sample 5 is placed in a sample container 4, and a coupler liquid 6 is provided for propagating the ultrasonic pulse between the acoustic lens 3 and the sample 5 in the sample container 4. The ultrasonic pulse incident on the sample 5 is reflected by the top, bottom or inside of the sample 5. Its reflected wave is again passed through the acoustic lens 3, converted into an electric signal by the transducer 2 and applied to a pre-amplifier 7. A gate section 8 is connected to the output side of the pre-amplifier 7. The gate section 8 serves to gate the received electric signal at such a timing that an output component which corresponds to the focus position of the acoustic lens 3 can be picked up from the signal. An attenuator 9 is connected to the gate section 8. The attenuation of this attenuator 9 is adjusted, as will be described later, to vary the ratio of its input and output. The output of the attenuator 9 is detected by a peak detector section 10. The output of the peak detector section 10 is applied to an input terminal of comparator 11 and also to an A/D converter section 12. A threshold value is applied from a threshold value level setting section 13 to another input terminal of the comparator 11. The comparator 11 produces an "ON" output only when the output or detected value of the peak detector section 10 exceeds the threshold value. Outputs of the comparator 11 and the A/D converter section 12 are applied to a computer 14. The acoustic lens 3 is moved in a direction in which the ultrasonic pulse enters into the acoustic lens 3, or in a direction Z, by a Z drive section 15. When a Z drive controller section 16 receives a command signal from the computer 14, it applies a drive signal to the Z drive section 15, which is made operative in response to this applied drive signal. Further, when an XY scanner section 17 receives an XY scanning signal from the computer 14, the sample 5 is scanned in directions X and Y by the XY scanner section 17. A pulse controller section 18 outputs a transmission trigger signal to the pulse transmitter section 1 in response to a transmission timing signal applied from the computer 14. A gate width adjuster section 19 is connected to the output of the pulse controller section 18 and the output of the computer 14 to adjust the gate width of the gate section 8 in response to a command applied from the computer 14.

When the transmission trigger signal is applied from the pulse controller section 18 to the pulse transmitter section 1, the pulse transmitter section 1 generates a single pulse signal, which is electro-acoustically converted into an ultrasonic pulse by the transducer 2. This ultrasonic pulse enters into the sample 5, passing through the acoustic lens 3. The reflected wave from the sample 5 is again passed through the acoustic lens 3 and converted into an electric (or received) signal by the transducer 2. On the other hand, the pulse controller section 18 outputs a pulse to the gate width adjuster section 19 at such a timing that can be calculated from the working distance which is a characteristic of the acoustic lens 3. Responsive to the pulse signal thus applied, the gate width adjuster section 19 outputs such a gate signal to the gate section 8 that has a pulse width large enough to cover dispersion in the working distance of the acoustic lens 3. Received electric signals applied from the pre-amplifier 7 are gated by the gate section 8 at the above calculated timing to pick up only those which correspond to waves reflected from the vicinity of an expected focus point on the sample 5. The signal thus picked up is applied to the attenuator 9 whose attenuation is set by the computer 14. The signal thus applied is, therefore, attenuated only by a computer-set amount by the attenuator 9. The output signal of the attenuator 9 is applied to the peak detector section 10 where its peak value is detected. The peak value of a signal outputted from the peak detector section 10 is compared with the threshold value by the comparator 11. When the signal passed through the attenuator 9 has a peak value larger than the threshold value, the comparator 11 output is "ON". The computer 14 adjusts, at all times, the attenuation of the attenuator 9 in such a way that the comparator 11 output is changed from "ON" to "OFF".

Figure 2:
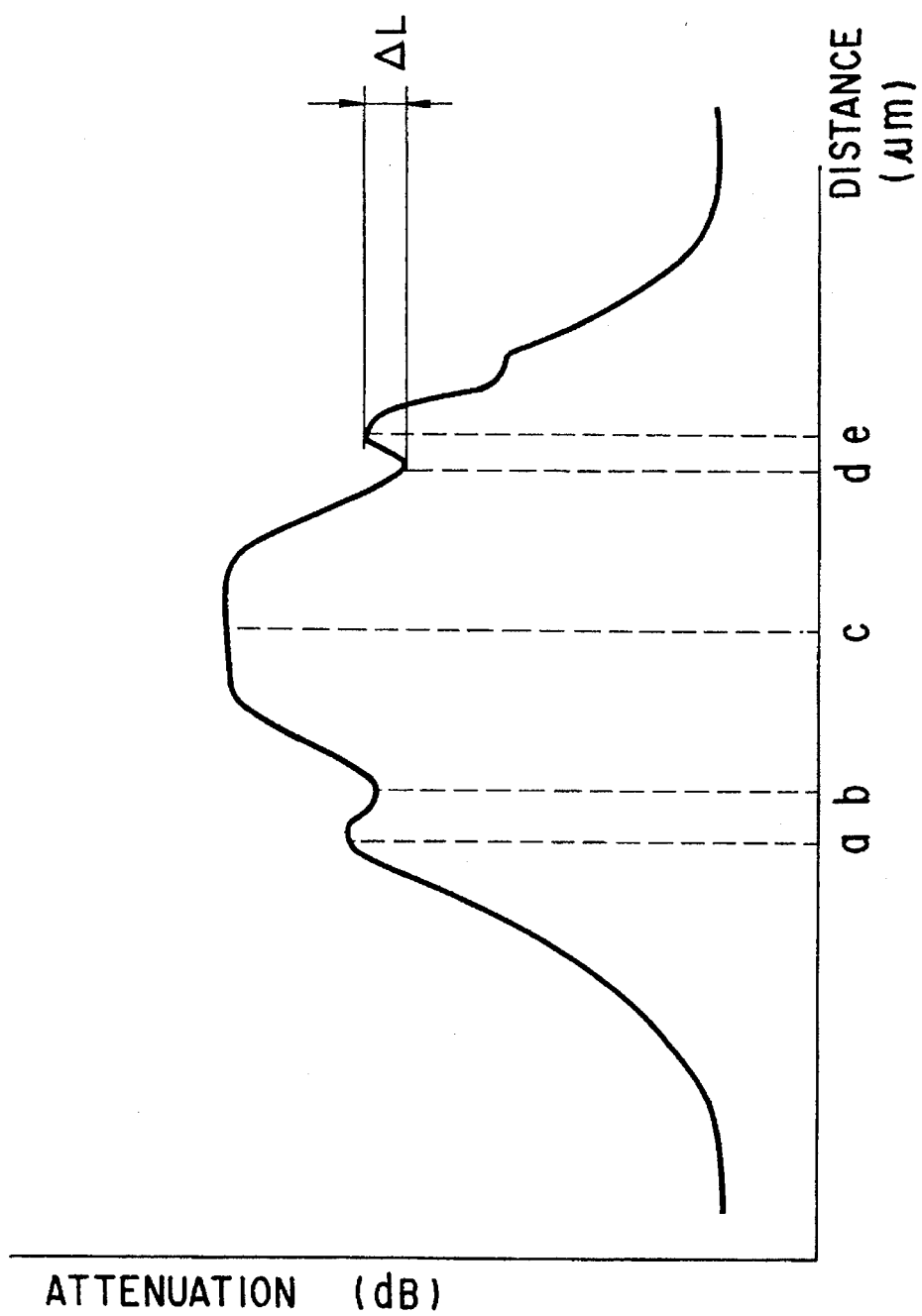
FIG. 2 is a graph showing an attenuation curve of the attenuator obtained when the acoustic lens is moved toward a sample in the embodying ultrasonic microscope.

FIG. 2 shows an example of attenuation change in the attenuator 9. This change is obtained when the acoustic lens 3 is moved from a position remote enough from the sample 5 to the sample 5 in the above-described case. The acoustic lens 3 is focused on the sample 5 near a distance (c). However, the strength of waves reflected from the sample near the focus point is quite large. The pre-amplifier 7 becomes saturated, and this keeps the attenuation at a certain value for a certain time period. Maximum points represented by (a) and (e) are created by noise and other factors.

The acoustic lens 3 is moved gradually little by little, from a position remote enough to the sample 5 to gain automatic focus. Every distance that the lens 3 is moved, the computer 14 adjusts the attenuation of the attenuator 9 to change the signal outputted by the comparator 11 from "ON" to "OFF". The largest attenuation seen until the lens 3 arrives at a current position is stored in the memory of the computer 14 and when the current attenuation is larger than that stored, the attenuation stored is updated. This attenuation updating is repeated and every time the attenuation updating is repeated, the position of the acoustic lens 3 is stored. When the current attenuation is equal to that stored, the memory in the computer 14 is not updated, but the acoustic lens 3 is further moved nearer to the sample 5. When the current attenuation is smaller than that stored, the following formula is used together with a value previously set in the memory of the computer 14.

$$(\text{current attenuation}) < (\text{attenuation stored}) - (\text{set value}) \qquad (1)$$

wherein the set value is intended to remove the influence of noise, as shown in FIG. 2, and it is set equal to or a little larger than a difference $\Delta L$ between attenuations at the distances (e) and (d). This set value is determined by examining noise characteristics and by other factors.

When the current attenuation does not meet the condition expressed by the formula (1), the acoustic lens 3 is still further moved nearer to the sample 5. And, when the condition is satisfied, the movement of the acoustic lens 5 is stopped.

When the movement of the acoustic lens 3 is stopped, that position of the acoustic lens 3 which corresponds to the attenuation stored in the memory of the computer 14 is (f) in FIG. 3 which is near to the focus point. On the other hand, that position at which the acoustic lens 3 is stopped is (g) in FIG. 3 where the attenuation becomes smaller than a value obtained by subtracting the set value from the largest attenuation. The focus position (c) is between the distances (f) and (g) at all times.

In order to calculate the focus position of the acoustic lens 3, an approximation is made from the distances (f) and (g). A focus position (c') is thus calculated. FIG. 4 shows the focus position (c') obtained by the approximation. The attenuation at this focus position (c') is larger than that at the distance (f) but smaller than the smallest step (or in FIG. 3) of changing values of the attenuation. It is, therefore, assumed that the attenuation at the focus position (c') is a value obtained by adding the one step of changing attenuations to the attenuation at the distance (f) and that the attenuation at the distance (g) is a value obtained by subtracting the above set value from the attenuation stored when the movement of the acoustic lens 3 is stopped. The focus position (c') at this time can be approximated by a secondary curve passing through points G and F and contacting a line (m), as shown in FIG. 4. Because the focus position (c') can be calculated by thins approximation, automatic focus adjustment is finished when the acoustic lens 3 is moved to the position (c').

When the acoustic lens 3 is operated as described above, it is focused on the sample 5. Acoustic lens 3 then stays at the position at which it is focused. Further, the attenuation is set to be the stored maximum attenuation described above as having been determined at a position f (see FIG. 3). While shifting little by little the timing at which the gating is carried out, the gating position at which the output signal applied from the comparator 11 is "ON" is then detected.

According to the above-described embodiment of the present invention, the wave components reflected from near the expected focus point on the sample 5 are picked up and the attenuation is adjusted to bring the input/output ratio of the attenuator 9 to a desirable value when the acoustic lens 3 is moved. The attenuating curve thus obtained enables the focus position to be obtained. Therefore, the focus position can be more easily detected without setting the threshold value near the strength of that wave reflected when the acoustic lens 3 is at its focus point, as seen in the conventional cases. The focus adjustment of the acoustic lens 3 can be therefore made extremely easier, thereby facilitating the operation of forming the ultrasonic image of any sample to a greater extent.

When reflected waves from the sample 5 are saturated in the pre-amplifier 7, a point which is lowered from the attenuation at the distance (g) by $\Delta l$ is measured and the secondary curve approximation is then carried out using three points. The focus position (c') can be thus obtained. The shape of a changing attenuation curve is determined by the frequency of the acoustic lens 3 and its angular aperture. When the attenuating curve is previously measured, therefore, the focus position can be obtained by the shape of the curve and by measuring two points in the same manner as in the above case.

When reflected waves from the sample 5 are not saturated in the pre-amplifier 7, attenuations of the attenuator and distances occurring at every attenuation until the acoustic lens 3 is moved from the distance (f) to the distance (g) are all stored in the memory of the computer 14. After the movement of the acoustic lens 3 is stopped, therefore, a distance which corresponds to the largest of the attenuations stored can be taken for the focus position. The focus adjustment can be thus achieved with a higher accuracy.

Further, when the gating width of the gate section 8 is made wider to pick up signals received, any acoustic lens of the same kind as the above-mentioned one can be used even if it is different in working distance. Furthermore, when the set value is adjusted, the automatic focusing can be achieved even if waves transmitted to the sample 5 are of the burst type.

Although the attenuation of the attenuator 9 has been controlled by the computer 14, a control circuit for feeding outputs of the comparator 11 back to the attenuator 9 may be used.

According to the ultrasonic microscope of the present invention, it is unnecessary for the operator to adjust the threshold value every time the sample is replaced by a new one and the automatic focusing can be more easily adjusted, thereby enhancing the utility of the microscope to a greater extent.

We claim:

1. An ultrasonic microscope wherein ultrasonic waves converged by an acoustic lens are made incident onto a sample, reflected waves from the sample are received and converted into received electric signals, and the ultrasonic wave image of the sample is formed using the received signals, comprising: a means for adjusting the distance of the acoustic lens relative to the sample; a means for picking up those of the received electric signals which correspond to a part of the reflected signals from the sample; an attenuator receiving an output signal from the pickup means; a means for storing a previously set threshold value; a means for comparing a peak value of an output of the attenuator with said previously-set threshold value so as to produce an "ON" output signal when the threshold value is exceeded; means for adjusting an attenuation amount of said attenuator so as to vary the signal input/output ratio of said attenuator in order to change the "ON" output signal of the comparing means to "OFF"; and means for calculating the focus position of said acoustic lens to produce a calculation result on the basis of an attenuation curve obtained as said attenuation amount with regard to one position of said acoustic lens when said acoustic lens is moved from another position to said one position, remote from its focus position, to said sample and for outputting a drive signal, responsive to said calculation result, to said distance adjuster means.

2. The ultrasonic microscope according to claim 1, wherein said pickup means includes a gate section for picking up only those signals which correspond to reflected waves from near an expected focus point on the sample, and means for setting the gating time of said gate section responsive to a signal applied from said means for calculating.

* * * * *